(12) United States Patent  
Janzig et al.

(10) Patent No.: US 8,131,370 B2
(45) Date of Patent: Mar. 6, 2012

(54) METHODS OF MANUFACTURING A HERMETIC LEAD CONNECTOR

(75) Inventors: Darren A. Janzig, Center City, MN (US); Gerald G. Lindner, Lino Lakes, MN (US); Chris J. Paidosh, St. Anthony, MN (US)

(73) Assignee: Medtronic, Inc, Minneapolis, MN (US)

( * ) Notice: Subject to any disclaimer, the term of this patent is extended or adjusted under 35 U.S.C. 154(b) by 776 days.

(21) Appl. No.: 11/733,243

(22) Filed: Apr. 10, 2007

(65) Prior Publication Data

US 2008/0208278 A1     Aug. 28, 2008

Related U.S. Application Data

(60) Provisional application No. 60/885,433, filed on Jan. 18, 2007.

(51) Int. Cl.
*A61N 1/375* (2006.01)

(52) U.S. Cl. .......................................... 607/37

(58) Field of Classification Search ............... 607/37
See application file for complete search history.

(56) References Cited

U.S. PATENT DOCUMENTS

| | | | |
|---|---|---|---|
| 4,934,366 A | 6/1990 | Truex | |
| 5,871,513 A * | 2/1999 | Taylor et al. | .................... 607/36 |
| 6,029,089 A | 2/2000 | Hawkins | |
| 6,327,502 B1 | 12/2001 | Johansson | |
| 6,498,952 B2 | 12/2002 | Imani | |
| 6,505,073 B2 | 1/2003 | Gramse | |
| 6,564,106 B2 * | 5/2003 | Guck et al. | .................... 607/116 |
| 6,654,641 B1 | 11/2003 | Froberg | |
| 6,816,745 B1 | 11/2004 | Brand | |
| 6,895,276 B2 | 5/2005 | Kast | |
| 6,934,588 B1 | 8/2005 | Brand | |
| 7,058,452 B2 | 6/2006 | Dahlberg | |
| 7,070,455 B2 | 7/2006 | Balsells | |
| 7,110,819 B1 | 9/2006 | O'Hara | |
| 7,447,533 B1 * | 11/2008 | Fang et al. | .................... 600/310 |
| 2002/0128692 A1 | 9/2002 | Imani | |
| 2003/0073348 A1 | 4/2003 | Ries | |

FOREIGN PATENT DOCUMENTS

| | | |
|---|---|---|
| WO | WO 90/02581 | 3/1990 |
| WO | WO 00/12174 | 3/2000 |
| WO | WO 03/075414 | 9/2003 |
| WO | WO 03/092808 | 11/2003 |

OTHER PUBLICATIONS

PCT International Search Report dated Oct. 24, 2007.
U.S. Appl. No. 11/733,240, filed Apr. 10, 2007, Janzig.
U.S. Appl. No. 11/733,245, filed Apr. 10, 2007, Janzig.
U.S. Appl. No. 11/733,247, filed Apr. 10, 2007, Janzig.

* cited by examiner

*Primary Examiner* — Carl H Layno
*Assistant Examiner* — Luther Behringer
(74) *Attorney, Agent, or Firm* — Mueting Raasch & Gebhardt PA

(57) ABSTRACT

A method of manufacturing a hermetic lead connector includes fixing an electrically insulating ring between an electrically conducting contact ring and an electrically conducting spacer ring to form a hermetic ring subassembly, and fixing a plurality of the hermetic ring subassemblies in axial alignment to form a hermetic lead connector. The hermetic lead connector includes an open end, an outer surface, and an inner surface defining a lead aperture. The hermetic lead connector provides a hermetic seal between the outer surface and the inner surface.

17 Claims, 8 Drawing Sheets

METHODS OF MANUFACTURING A HERMETIC LEAD CONNECTOR

CROSS-REFERENCE TO RELATED APPLICATION

This application claims the benefit of priority to U.S. Provisional Application No. 60/885,433, entitled "INTERNAL HERMETIC LEAD CONNECTOR FOR IMPLANTABLE DEVICE" filed on Jan. 18, 2007, the disclosure of which is incorporated herein by reference.

FIELD

The present disclosure relates to method of manufacturing an internal hermetic lead connector for an implantable device and particularly to method of manufacturing an active medical implantable device having a lead connector disposed within the hermetic housing of the device.

BACKGROUND

Implantable active medical devices, such as cardiac rhythm management devices (pacemakers and defibrillators) and a variety of implantable muscle/nerve stimulators generally include a battery and battery-powered electronic pulse generator contained within a hermetically sealed housing or case and attached to a lead connector housing or lead connector block. The lead connector block is often affixed to the hermetically sealed housing with brackets, metal solder, and/or a medical grade adhesive.

The electronics within the hermetically sealed housing are conductively coupled to the lead connector block with an electrical feedthrough assembly. Electrical feedthroughs serve the purpose of providing a conductive path extending between the interior of a hermetically sealed container and a point outside the hermetically sealed housing. The conductive path through the feedthrough usually includes a conductor pin or terminal that is electrically insulated from the hermetically sealed housing. Many such feedthroughs are known in the art that provide the conductive path and seal the electrical container from its ambient environment. Such feedthroughs typically include a ferrule, and an insulative material such as a hermetic glass or ceramic seal that positions and insulates the pin within the ferrule. Sometimes it is desired that the electrical device include a capacitor within the ferrule and around the terminal, thus shunting any electromagnetic interference (EMI) at high frequencies at the entrance to the electrical device to which the feedthrough device is attached. Typically, the capacitor electrically contacts the pin lead and the ferrule. While this arrangement has proven to be highly reliable, it involves a variety of expensive manufacturing processes and parts that necessarily increase the cost of the resulting product.

Ongoing efforts by the industry to reduce the size of the implantable device are desired. Early implantable pacemakers back in the 1960's were about the size of a hockey puck. With advances in microelectronics and integrated circuitry, significantly more features and capabilities have been embodied in implantable active medical devices capable of sizes as small as about 10 cc. Nonetheless, efforts to further reduce the size of implantable active medical devices continue in the industry.

BRIEF SUMMARY

The present disclosure relates to methods of manufacturing an internal hermetic lead connector for an implantable device and particularly to methods of manufacturing an active medical implantable device having a lead connector disposed within the hermetic housing of the device.

In a first embodiment, a method of manufacturing a hermetic lead connector includes fixing an electrically insulating ring between an electrically conducting contact ring and an electrically conducting spacer ring to form a hermetic ring subassembly, and fixing a plurality of the hermetic ring subassemblies in axial alignment to form a hermetic lead connector. The hermetic lead connector includes an open end, an outer surface, and an inner surface defining a lead aperture. The hermetic lead connector provides a hermetic seal between the outer surface and the inner surface.

In another embodiment, a method of manufacturing an implantable active medical device includes providing an active medical device housing defining a housing interior, a power source and electronics in electrical communication are disposed within the housing interior, and fixing a hermetic lead connector to the active medical device housing. The lead connector projecting into the housing interior and having an open end projecting through the active medical device housing. The lead connector includes an outer surface and an inner surface defining a lead aperture, the lead connector comprising one or more electrically conducting contact rings spaced apart by electrically insulating rings. The one or more electrically conducting contact rings in electrical communication with the electronics, and the lead connector providing a hermetic seal between the lead connector outer surface and the lead connector inner surface.

In a further embodiment, a method of manufacturing an implantable active medical device includes disposing a hermetic lead connector into an active medical device housing. The active medical device housing defining a housing interior, a power source and electronics in electrical communication are disposed within the housing interior. The lead connector having an open end projecting through the active medical device housing. The lead connector including an outer surface and an inner surface defining a lead aperture. The lead connector having one or more electrically conducting contact rings spaced apart by electrically insulating rings. The one or more electrically conducting contact rings in electrical communication with the electronics, and the lead connector provides a hermetic seal between the lead connector outer surface and the lead connector inner surface.

BRIEF DESCRIPTION OF THE DRAWINGS

The invention may be more completely understood in consideration of the following detailed description of various embodiments of the invention in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
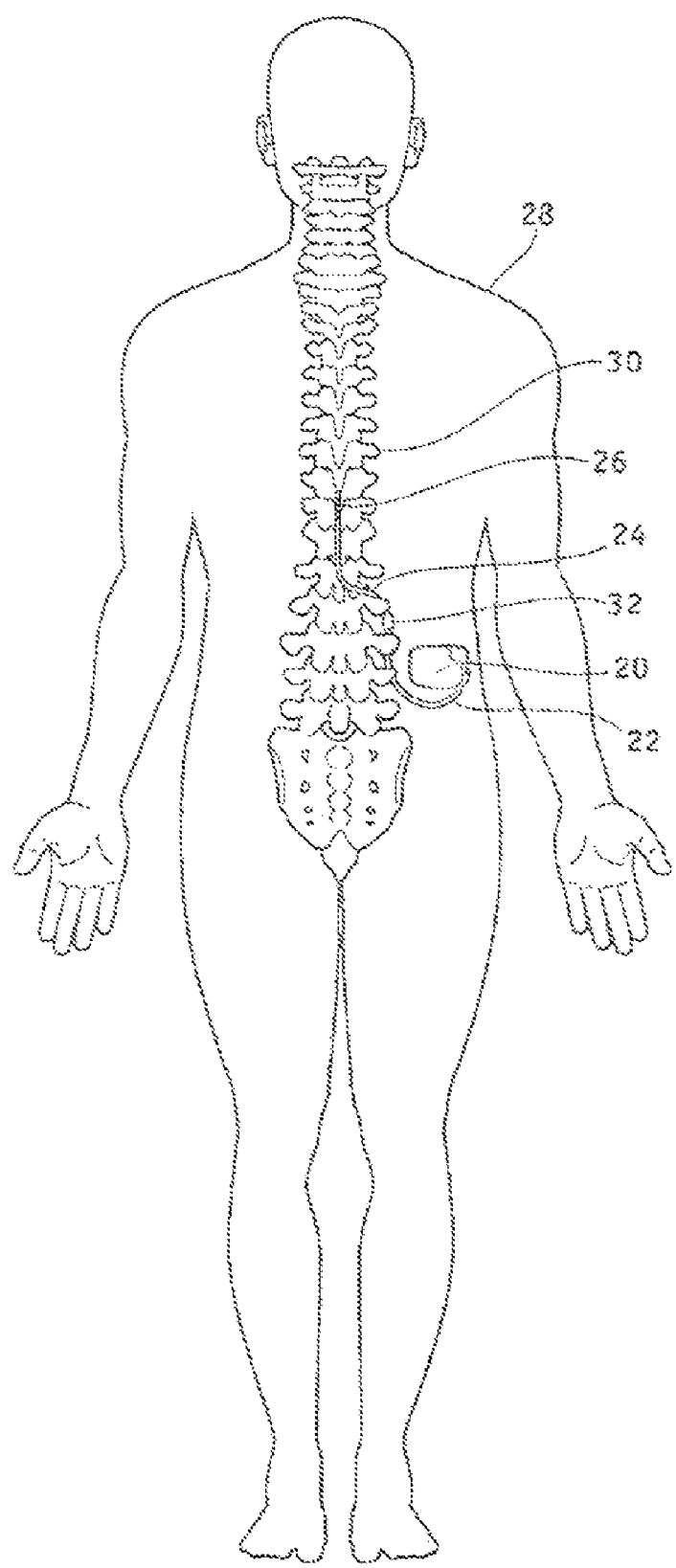
FIG. 1 is a schematic diagram of a an active medical device implanted within a human body.

In the following description, reference is made to the accompanying drawings that form a part hereof, and in which are shown by way of illustration several specific embodiments. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The term "active implantable medical device" or "implantable signal generator" are used interchangeably and includes, for example, a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, and the like.

The term "hermetic seal", "hermetically sealed" are used interchangeably and refer to an airtight seal. This term is often used to describe electronic parts that are designed and intended to secure against the entry of microorganisms, water, oxygen, and the like, and to maintain the safety and quality of their contents.

The present disclosure relates to methods of manufacturing an internal hermetic lead connector for an implantable device and particularly to methods of manufacturing an active medical implantable device having a lead connector disposed within the hermetic housing of the device. The internal hermetic lead connector allows electronics within the hermetic housing of the device to be directly coupled to the lead connector, thus a separate attached conventional feedthrough connector block is not needed. Elimination of the separate feedthtough connector block reduces the number of parts and connections needed to assemble the active medical implantable device and can reduce the overall size of the active medical device. While the present invention is not so limited, an appreciation of various aspects of the invention will be gained through a discussion of the examples provided below.

FIG. 1 is a schematic diagram of an active medical device 20 implanted within a human body or patient 28. The implanted active medical device 20 is illustrated as a neurostimulator, however, the implanted active medical device 20 can be any "active implantable medical device" or "implantable signal generator" as described above and can be placed in any location within a body cavity or tissue within the body, or on the surface of a patient's skin, as desired.

The active medical device 20 is coupled to a lead extension 22 having a proximal end coupled to the active medical device 20, and a lead 24 having a proximal end coupled to a distal end 32 of the lead extension 22 and a distal end of the lead 24 coupled to one or more electrodes 26. In other embodiments, the lead 24 proximal end is coupled to the active medical device 20, without a need for a lead extension 22. The active medical device 20 can be implanted in any useful region of the body such as in the abdomen of a patient 28, and the lead 24 is shown placed somewhere along the spinal cord 30. In many embodiments, the active medical device 20 has one or two leads each having four to eight electrodes. Such a system may also include a physician programmer and a patient programmer (not shown). The active medical device 20 can be considered to be an implantable signal generator of the type available from Medtronic, Inc. and capable of generating multiple signals occurring either simultaneously or one signal shifting in time with respect to the other, and having independently varying amplitudes and signal widths. The active medical device 20 contains a power source and the electronics for sending precise, electrical signals to the patent to provide the desired treatment therapy. While the active medical device 20, in many embodiments, provides electrical stimulation by way of signals, other forms of stimulation may be used as continuous electrical stimulation.

In many embodiments, the lead 24 is a wire having insulation thereon and includes one or more insulated electrical conductors each coupled at their proximal end to a connector and to contacts/electrodes 26 at its distal end. Some leads are designed to be inserted into a patient percutaneously (e.g. the Model 3487A Pisces—Quad® lead available from Medtronic, Inc.), and some are designed to be surgically implanted (e.g. Model 3998 Specify® lead, also available form Medtronic, Inc.). In some embodiments, the lead 24 may contain a paddle at its distant end for housing electrodes 26. In many embodiments, electrodes 26 may include one or more ring contacts at the distal end of lead 24.

Figure 2:
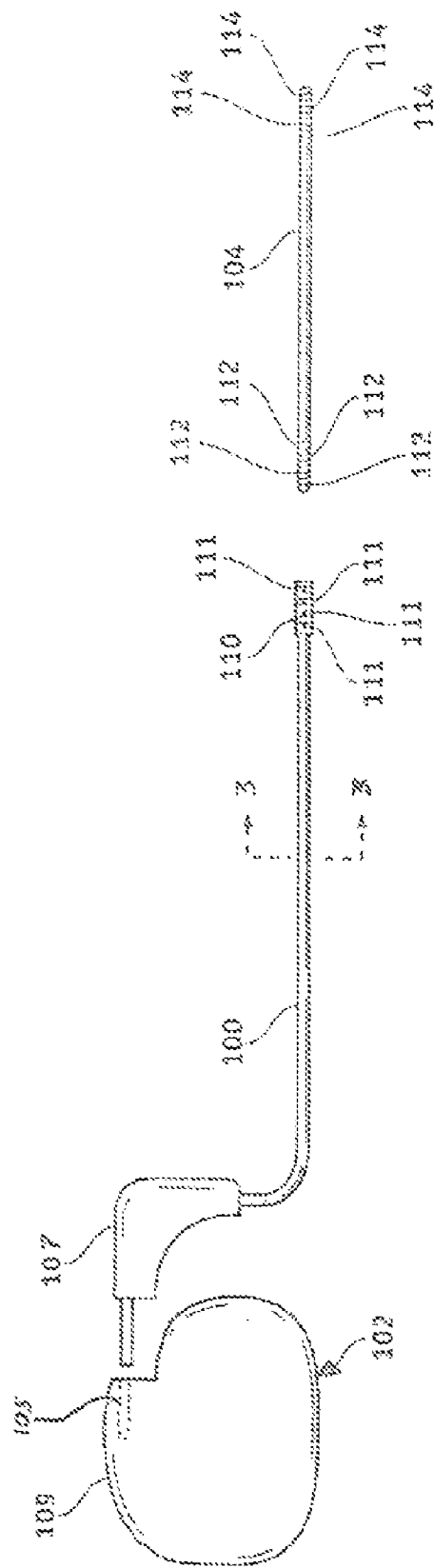
FIG. 2 is a schematic exploded view of an implantable active medical device.
Figure 3:
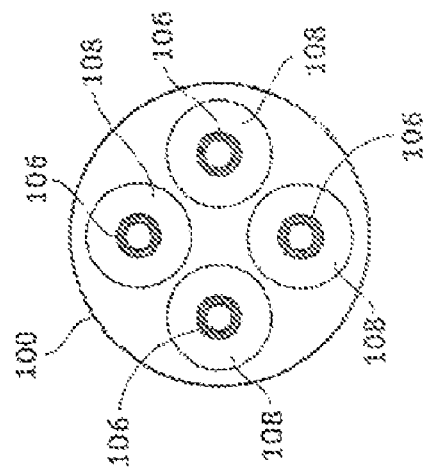
FIG. 3 is a schematic cross-sectional view of an lead body shown in FIG. 2 taken along line 3-3.

FIG. 2 is a schematic exploded view of the implantable active medical device described above and FIG. 3 is a schematic cross-sectional view of the lead extension body 100 shown in FIG. 2 taken along line 3-3. The implantable active medical device 102 can be coupled to a lead extension 100 configured to be coupled between an implantable active medical device 102 and the lead 104. The proximal portion of lead extension 100 includes a lead connector 107 configured to be received or plugged into housing lead connector 105 of the implantable active medical device 102 through a hermetically sealed housing 109 of the implantable active medical device 102. The distal end of extension 100 includes a connector 110 including internal contacts 111 and is configured to receive the proximal end of lead 104 having contacts 112 thereon. The distal end of lead 104 includes distal electrodes 114 that are in electrical connection with corresponding contacts 112.

In some embodiments, lead extension 100 can differ from lead 104 in that each conductor 106 in the lead body is helically wound or coiled in its own lumen 108 and not co-radially wound with the rest of the conductors as can be the case in lead 104.

Figure 4A:
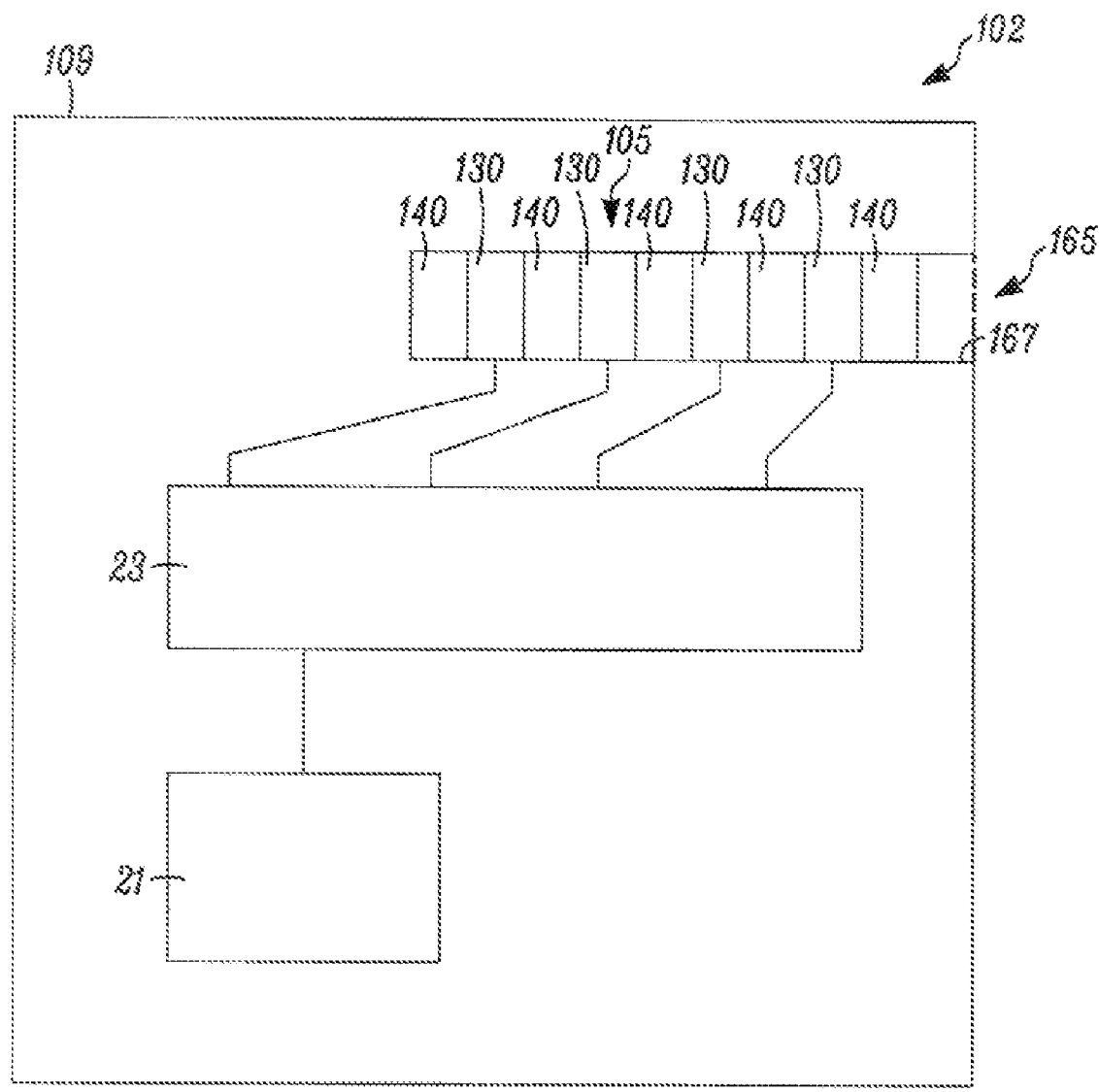
FIG. 4A is a schematic diagram cross-sectional view of an illustrative active medical device.

FIG. 4A is a schematic diagram cross-section view of an illustrative active medical device 102. The active medical device 102 includes a hermetically sealed housing 109 defining a sealed housing interior. A power source 21 and electronics 23 are in electrical communication and are disposed within the sealed housing 109 interior. A lead connector 105 projects into the sealed housing 109 interior and has an inner surface 167 defining a lead aperture 165.

Figure 4B:
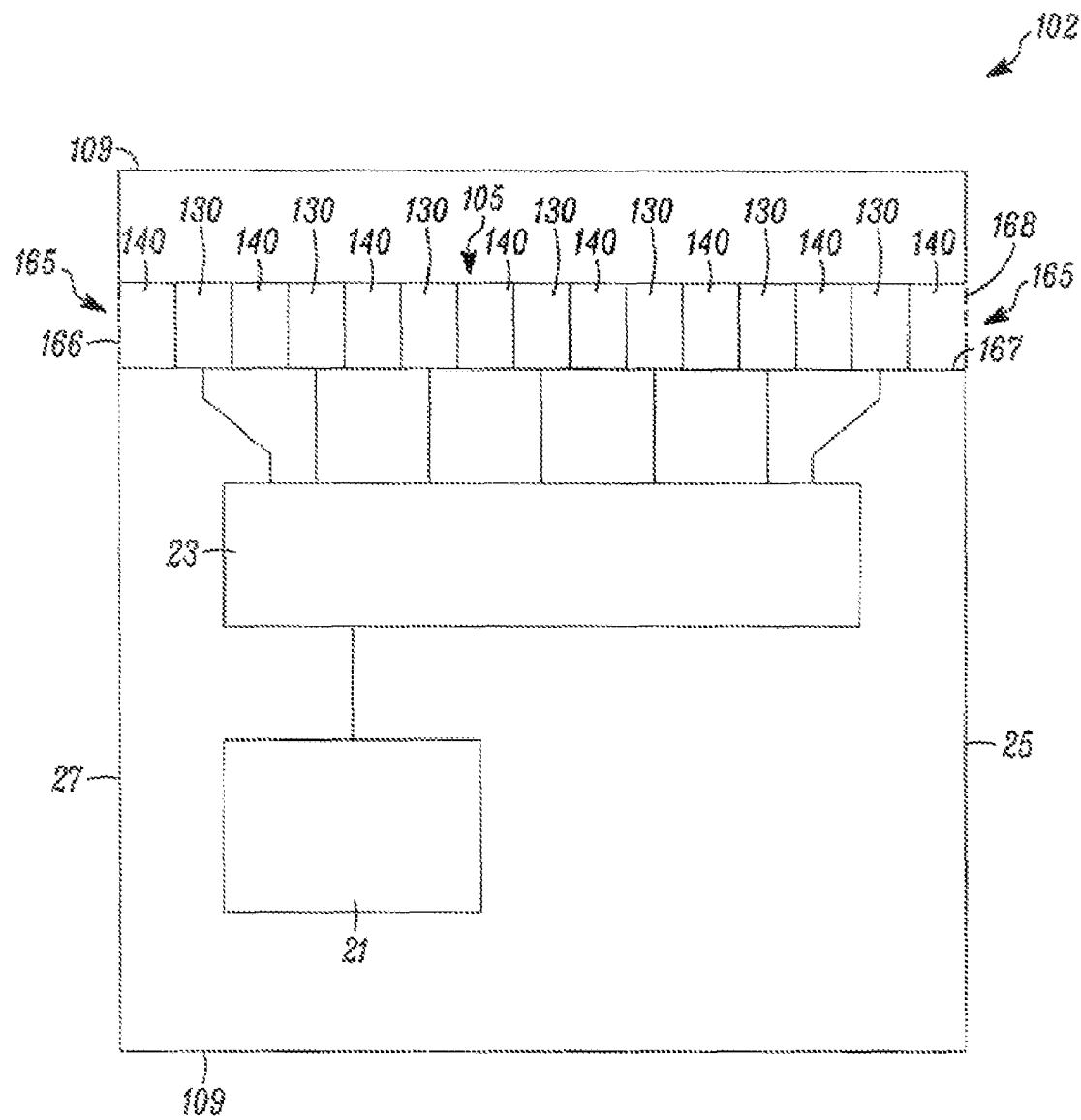
FIG. 4B is a schematic diagram cross-sectional view of another illustrative active medical device.

FIG. 4B is a schematic diagram cross-section view of an illustrative active medical device 102. The active medical device 102 includes a hermetically sealed housing 109 defining a sealed housing interior. A power source 21 and electronics 23 are in electrical communication and are disposed within the sealed housing 109 interior. A lead connector 105 projects into and through the sealed housing 109 interior and has an inner surface 167 defining an open lumen lead aperture 165.

The hermetically sealed housing 109 includes a first surface 27 and an opposing second surface 25. The lead connector 105 projects through the hermetically sealed housing 109 from the first surface 24 to the opposing second surface 25. Thus the lead connector 105 forms an open-ended lumen through the hermetically sealed housing 109 where the lead connector 105 has a first open end 166 at the first surface 24 and a second open end 168 at the second surface 25.

The lead connector 105 includes one or more electrically conducting contact rings 130 spaced apart by one or more electrically insulating rings 140. The one or more electrically conducting contact rings 130 are in electrical communication with the electronics 23 and the lead connector 105 provides a hermetic seal between the sealed housing 109 interior and the lead aperture 165. The electronics 23 generally control the active medical device 102. The power source 21 can be any useful battery or power source such as an inductive coil. In some embodiments, the electronics 23 includes memory. The memory can be any magnetic, electronic, or optical media, such as random access memory (RAM), read-only memory (ROM), electronically-erasable programmable ROM, flash memory, or the like.

The one or more electrically conducting contact rings 130 can be formed of any useful electrically conductive material. In many embodiments, the one or more electrically conducting contact rings 130 are formed of a metallic material such as, for example, titanium, stainless steel, MP35N, niobium, tantalum, platinum, and alloys or combinations thereof In some embodiments, the one or more electrically conducting contact rings 130 are formed of a metallic material such as, for example, titanium.

The electrically insulating rings 140 can be formed of any useful electrically insulating material. In many embodiments, the one or more electrically insulating rings 140 are formed of a single crystal sapphire, a polycrystalline or single crystal ceramic, or glass. In some embodiments, the one or more electrically insulating rings 140 are formed of a single crystal sapphire.

In some embodiments, a filtering capacitor is disposed between the electrically conducting contact rings 130 and the electronics 23. The filtering capacitor can effectively filter out undesirable electromagnetic interference (EMI) from the active medical device 102.

The implantable active medical device described herein can eliminate the need for a conventional separate feedthrough block that electrically connects a conventional lead connector block with the hermetically sealed electronics of the implantable active medical device. By placing the lead connector within the hermetically sealed active medical device housing, a direct electrical connection between the lead connector and the electronics can be made. In addition, the elimination of a feedthrough can reduce the size and volume of the implantable active medical device and can also reduce the number of parts and connections needed to assemble the implantable active medical device.

Figure 5:
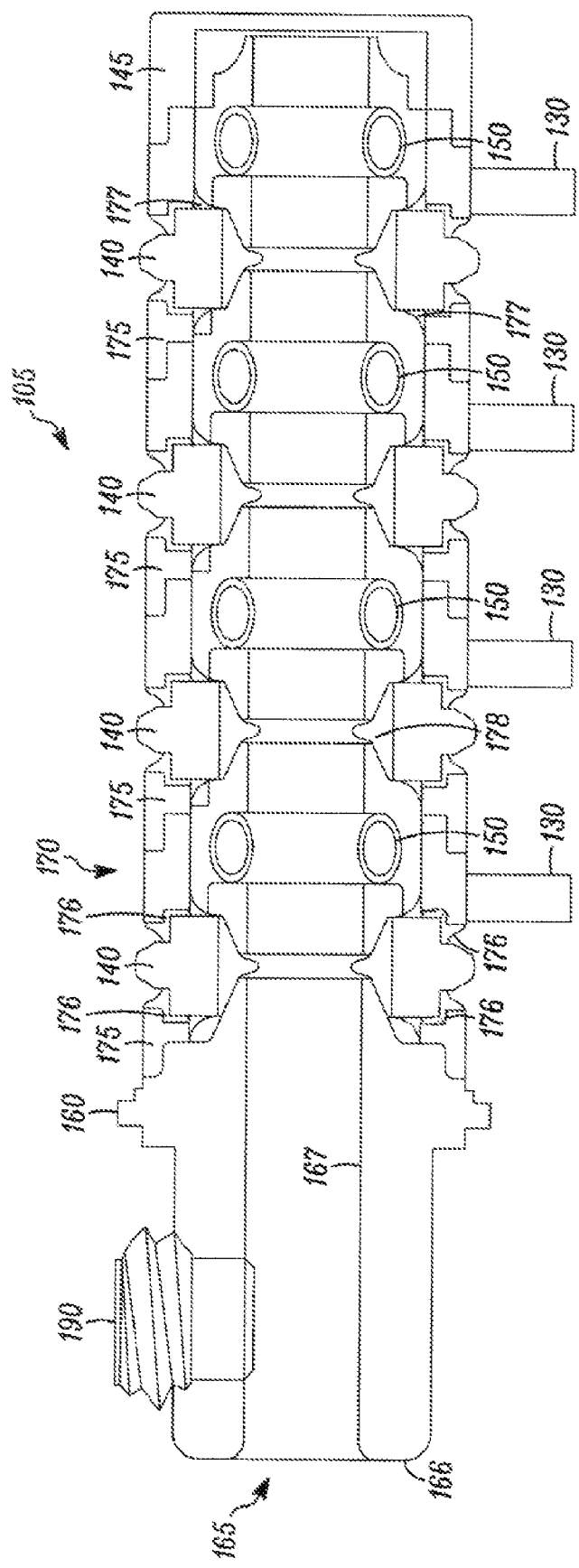
FIG. 5 is a schematic cross-sectional view of an illustrative lead connector.
Figure 6:
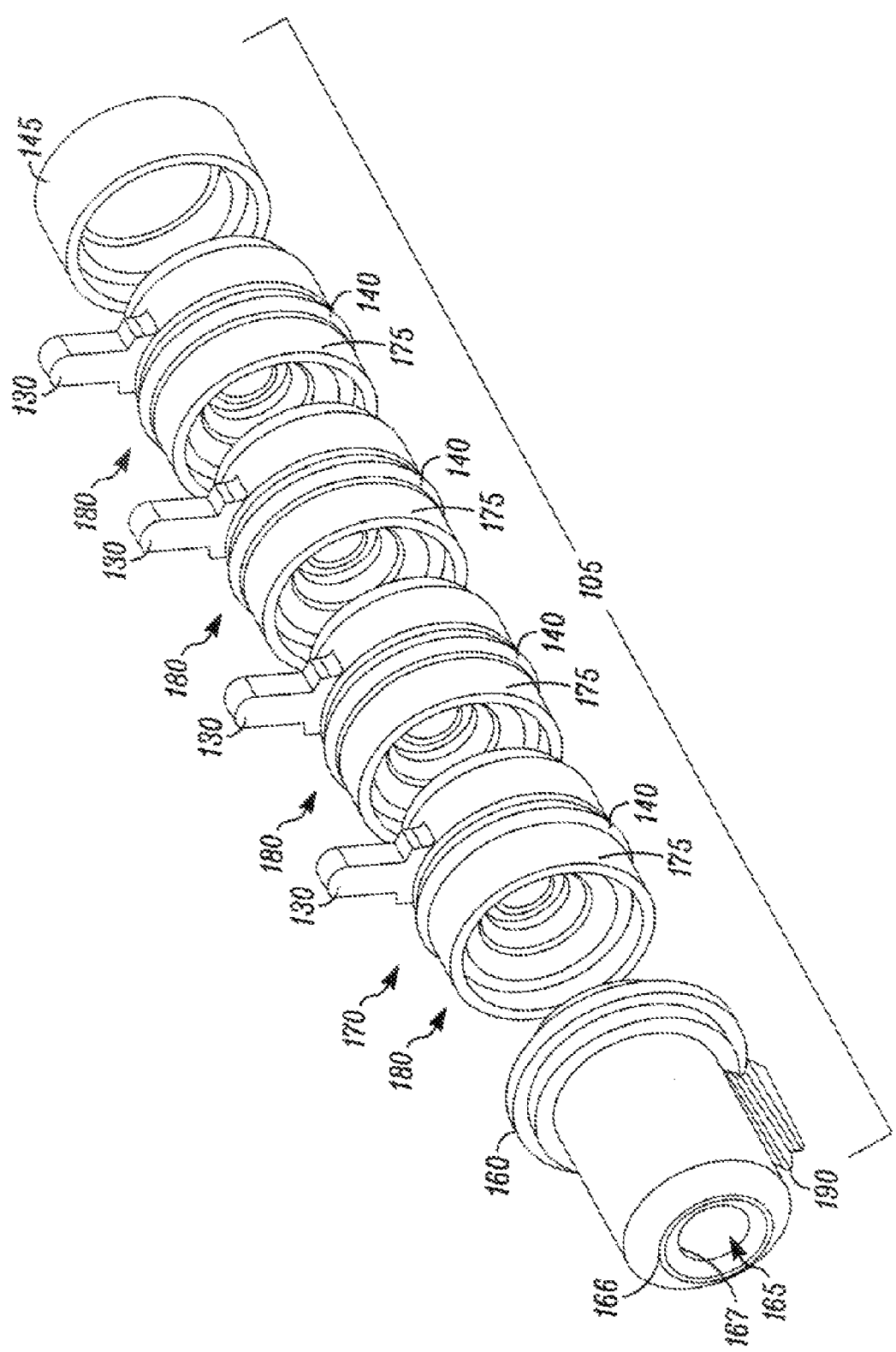
FIG. 6 is an exploded perspective view of the illustrative lead connector shown in FIG. 5.

FIG. 5 is a schematic cross-sectional view of an illustrative lead connector 105. FIG. 6 is an exploded perspective view of the illustrative lead connector 105 shown in FIG. 5. The illustrated lead connector 105 is an elongate member extending between a lead aperature 165 open end 166 and a lead connector cap 145, and having an inner surface 167 defining a lead aperture 165. The lead aperture 165 is configured to accept a lead or lead extension, as described above, and electrically couple one or more lead contacts with one or more connector contacts 130 that form the elongate body of the lead connector 105, that in many embodiments is generally cylindrical.

In many embodiments, the lead aperture 165 is a cylindrical lumen of generally circular cross-sectional area formed by an inner surface of the electrically conducting rings 130 and electrically insulating rings 140 welded or brazed together in axial alignment. The lead connector 105 defines a lead connector outer surface 170 and at least a portion of the lead connector outer surface 170 is disposed within the sealed housing 109 interior. In many embodiments, at least a majority of the lead connector outer surface 170 is disposed within the sealed housing 109 interior. In many embodiments, substantially the entire lead connector outer surface 170 is disposed within the sealed housing 109 interior. In some embodiments, the entire lead connector outer surface 170 is disposed within the sealed housing 109 interior.

In the illustrated embodiment, the lead connector 105 is formed of one or more electrically conducting contact rings 130 spaced apart by one or more electrically insulating rings 140. The one or more electrically conducting contact rings 130 are in electrical communication with the electronics (described above), and the lead connector 105 body provides a hermetic seal between the sealed housing interior/lead connector outer surface 170 and the lead aperture 165. The one or more electrically conducting contact rings 130 and one or more electrically insulating rings 140 are assembled in axial alignment to form the lead connector 105.

The one or more electrically conducting contact rings 130 can include one or more additional contact elements in electrical contact with and optionally disposed within each of the one or more electrically conducting contact rings 130. These one or more additional contact elements are configured to provide electrical communication between one or more electrically conducting contact rings 130 and a lead contact received within the lead aperture 165. In many embodiments, these contact elements are electrically conductive and resilient to provide an interference fit between the electrically conducting contact ring 130 and lead contact received within the lead aperture 165.

Examples of contact elements include, but are not limited to, spring elements. In many embodiments, the contact element includes an annular helical coil 150 (i.e., continuous coil spring 150) is disposed adjacent an inner surface of the electrically conducting contact ring 130. The helical annular coil 150 can be formed of any useful electrically conductive material such as, for example, a metal like gold, silver, titanium and the like. When a lead in inserted into the lead aperture 165, the lead and lead contact(s) can deflect the annular helical coil 150 and form an electrical contact between the lead contact and the electrically conducting contact ring 130. The continuous coil spring 150 provides a frictional electrical and mechanical engagement with a lead contact and the adjacent electrically conducting contact ring 130.

A mounting flange 160 can be fixed to the lead connector 105 adjacent the open end 166. The mounting flange 160 can be brazed or welded to the hermetically sealed housing 109. In many embodiments, the mounting flange 160 is brazed or welded to an exterior surface of the hermetically sealed housing 109. In other embodiments, the mounting flange 160 is brazed or welded to an interior surface of the hermetically sealed housing 109. A retention member 190 such as for example, a set screw, can be disposed on the lead connector 105 adjacent to the open end 166 and can assist in mechanical retention of a lead disposed within the lead aperture 165.

Figure 7:
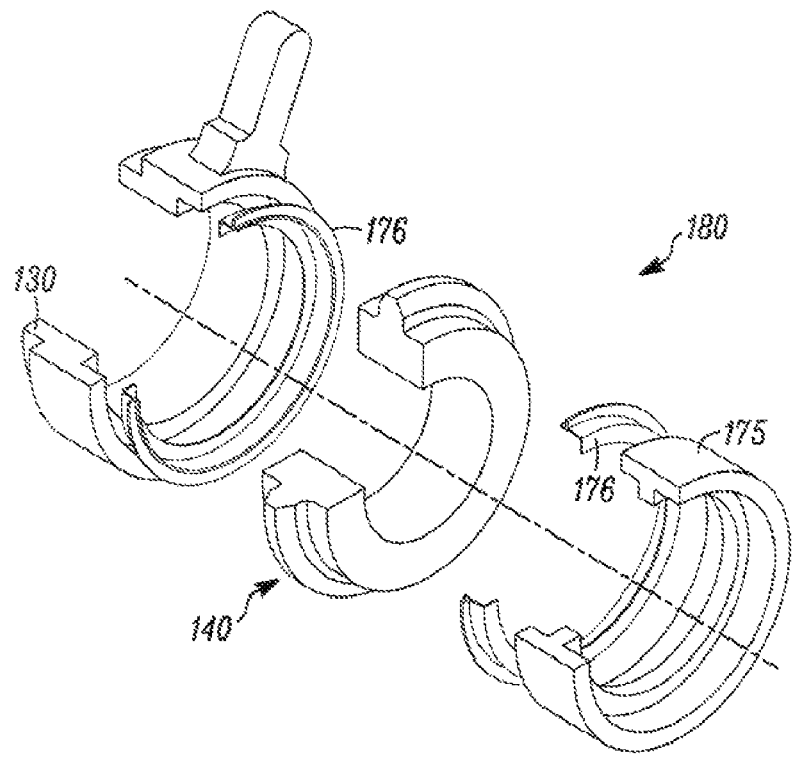
FIG. 7 is an exploded perspective cut-away view of the illustrative subassembly shown in FIG. 6.
Figure 8:
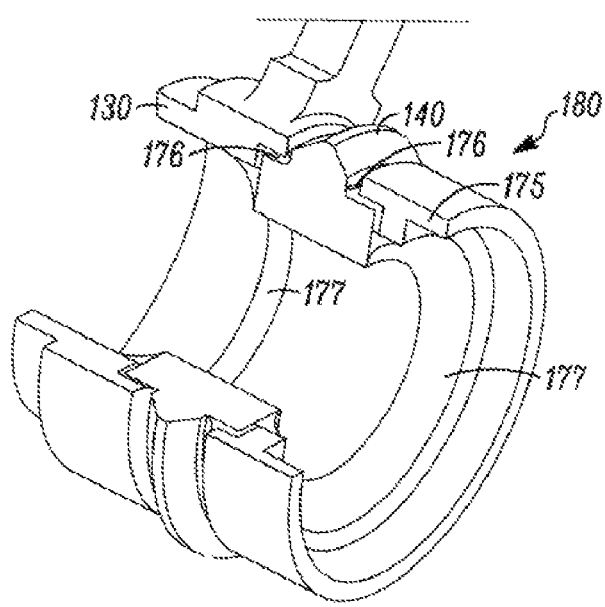
FIG. 8 is a perspective cut-away view of the illustrative subassembly shown in FIG. 6.

The lead connector 105 can be formed by any useful method. In many embodiments, the lead connector 105 is formed by assembling two or more lead connector subassemblies 180. FIG. 7 is an exploded perspective cut-away view of the illustrative subassembly 180 shown in FIG. 6. FIG. 8 is a perspective cut-away view of the illustrative subassembly 180 shown in FIG. 6.

Each lead connector subassembly 180 includes the electrically insulating ring 140 fixed between the electrically conducting contact ring 130 and an attachment ring or electrically conducting spacer ring 175. Thus, the electrically conducting spacer ring 175 is affixed to a first side of the electrically insulating ring 140 and the electrically conducting contact ring 130 is affixed to a second opposing side of the electrically insulating ring 140. The lead connector subassembly 180 includes the electrically insulating ring 140 brazed between the electrically conducting contact ring 130 and the electrically conducting spacer ring 175, leaving braze 176 disposed between the electrically insulating ring 140 and the electrically conducting contact ring 130, and between the electrically insulating ring 140 and the electrically conducting spacer ring 175. The braze 176 assists in providing the hermetic seal between the the sealed housing interior/lead connector outer surface 170 and the lead aperture 165. To form each subassembly, the electrically insulating ring 140 can be metallized on opposing edges and then the metallized edges are brazed (using braze 176) to the electrically conducting contact ring 130, and attachment ring or electrically conducting spacer ring 175.

The electrically conducting spacer ring 175 can be formed of can be formed of any useful electrically conductive material. In many embodiments, the electrically conducting spacer ring 175 is formed of a metallic material such as, for example, titanium, stainless steel, MP35N, niobium, tantalum, platinum, and alloys or combinations thereof. In some embodiments, the one electrically conducting spacer ring 175 is formed of a metallic material such as, for example, titanium.

In one embodiment, each ring subassembly includes an electrically insulating ring formed of a single crystal sapphire material and fixed between an electrically conducting contact ring formed of titanium and an electrically conducting spacer ring formed of titanium.

In many embodiments, a fluid seal material 177 is disposed on the exposed braze 176 joints within the lead aperture 165. The fluid seal material 177 can be any useful fluid sealing material that prevents moisture from contacting the exposed braze 176 joint within the lead aperture 165. The fluid seal material 177 provides braze joint corrosion protection. Useful fluid sealing material includes, for example, silicone, rubber, polymers, and the like. In many embodiments, the fluid sealing material 177 has a glass transition temperature less than the glass transition temperature of the braze 176. In embodiments that use non-corrosive braze 176, a fluid seal material 177 is not utilized.

In many embodiments, the brazing process is operated at temperatures above 1000 degrees centigrade. At these elevated temperatures, some elements that form the lead connector, described herein, are damaged, destroyed, or lose physical properties. For example, the contact element coil will lose its temper at brazing temperatures and the fluid and wiper seals will melt at brazing temperatures. Thus, the design and manufacturing method described herein allows for the lead connector elements that can withstand the brazing process only to be subjected to the brazing process and then the other temperature sensitive elements are assembled to form the lead connector.

Figure 9:
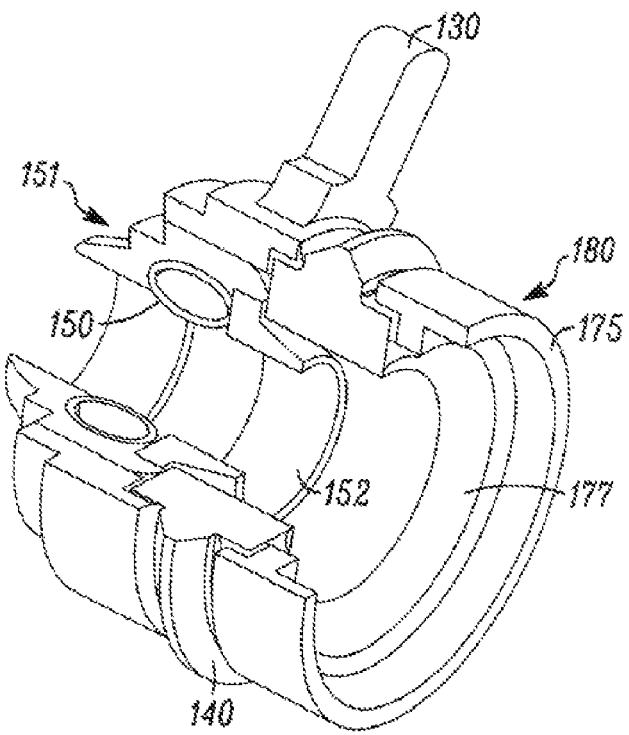
FIG. 9 is a perspective cut-away view of the illustrative subassembly shown in FIG. 6.
Figure 10:
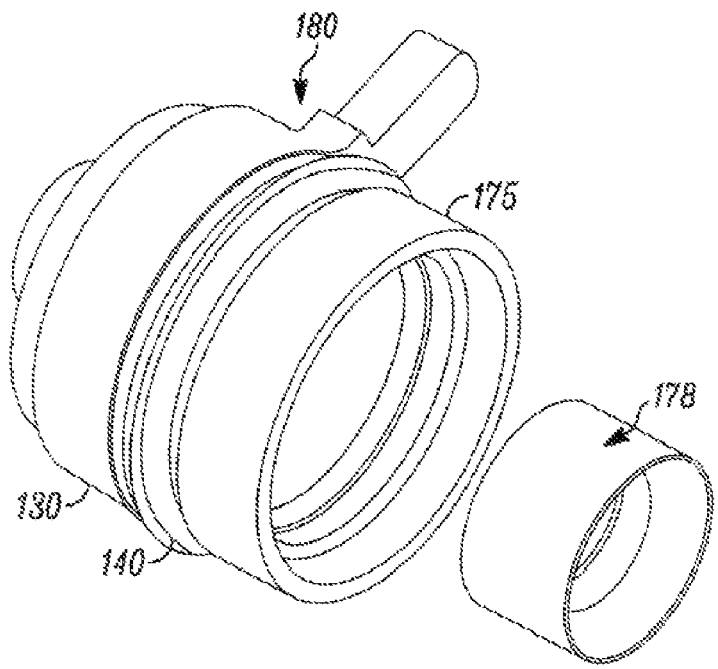
FIG. 10 is a perspective view of the illustrative subassembly shown in FIG. 6.

FIG. 9 is an perspective cut-away view of the illustrative subassembly 180 shown in FIG. 6. FIG. 10 is a perspective view of the illustrative subassembly 180 shown in FIG. 6. Each subassembly 180 can include additional elements such as, for example, a contact element 151, a wiper seal 178 or other sealing rings 152. In the illustrated embodiments, an annular helical coil 150 is disposed within a contact assembly 151 and the contact assembly is disposed within the electrically conducting contact ring 130. One useful contact assembly is a Bal Seal contact ring assembly available from Bal Seal Engineering Co., Inc., (Foothill Ranch, Calif.) The contact assembly can be welded to the electrically conducting contact ring 130. This method of fabrication of the individual subassembly 180 allows the body of the subassembly 180 to be brazed together at brazing temperatures and then temperature sensitive components (such as the contact assembly 151, fluid seal material 177 and wiper seal 178) can be installed into the subassembly 180 following the brazing process.

The wiper seal or sealing rings can be formed of any useful electrically insulating material, and is often deformable. The wiper seal and sealing rings can assist in electrically isolating adjacent electrically conducting contact rings 130. Each lead connector subassembly 180 can be welded together in axial alignment using conventional techniques. Thus, a first ring subassembly electrically conducting contact ring is welded to an adjacent second ring subassembly electrically conducting spacer ring. As illustrated, in many embodiments, each ring subassembly has substantially similar dimensions. Thus, the plurality of ring subassemblies can be stacked and fixed in any useful number of ring subassemblies providing a modular design.

The lead connectors described herein, are directly coupled to electronics within the housing hermetic seal and since both the lead connector and the electronics are within the housing hermetic seal, a conventional feedthrough connector or separate lead connector block is not needed to electrically couple the lead connector to the electronics. These features allow the active medical device to be assembled with fewer parts, fewer connections and to form an overall smaller active medical device than a device where the lead connector is not formed within the hermetic seal of the active medical device housing.

Thus, embodiments of the METHODS OF MANUFACTURING A HERMETIC LEAD CONNECTOR are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method of manufacturing a hermetic lead connector comprising:
brazing an electrically insulating ring between an electrically conducting contact ring and an electrically conducting spacer ring to form a hermetic ring subassembly;
installing a fluid seal or wiper seal within the hermetic ring subassembly, wherein the fluid seal or wiper seal assists in electrically isolating adjacent electrically conducting contact rings; and
fixing a plurality of the hermetic ring subassemblies in axial alignment to form a hermetic lead connector, the hermetic lead connector comprising an open end, an outer surface, and an inner surface defining a hermetic lead aperture and the hermetic lead connector provides a hermetic seal between the outer surface and the inner surface; wherein the brazing assists in providing a hermetic seal between the lead connector outer surface and the lead aperture.

2. A method according to claim 1, wherein the fixing an electrically insulating ring between an electrically conducting contact ring and an electrically conducting spacer ring comprises fixing an electrically insulating ring comprising a single crystal sapphire material between an electrically conducting contact ring comprising titanium and an electrically conducting spacer ring comprising titanium.

3. A method according to claim 1, further comprising disposing a fluid seal material on brazed joints within the hermetic ring subassembly before the fixing of the plurality of the hermetic ring subassemblies in axial alignment.

4. A method according to claim 1, further comprising disposing a helical annular coil within the hermetic ring subassembly before the fixing of the plurality of the hermetic ring subassemblies in axial alignment.

5. A method according to claim 1, wherein the fixing a plurality of the hermetic ring subassemblies in axial alignment to form a hermetic lead connector comprises welding a plurality of the hermetic ring subassemblies in axial alignment to form a hermetic lead connector.

6. A method according to claim 1, wherein the fixing a plurality of the hermetic ring subassemblies in axial alignment to form a hermetic lead connector comprises fixing a first ring subassembly electrically conducting contact ring to an adjacent second ring subassembly electrically conducting spacer ring.

7. A method according to claim 1, wherein fixing a plurality of the hermetic ring subassemblies in axial alignment to form a hermetic lead connector comprises fixing a plurality of the hermetic ring subassemblies each having substantially similar dimensions in axial alignment to form a hermetic lead connector comprising an open end, an outer surface, and an inner surface defining a lead aperture having a substantially uniform diameter and the hermetic lead connector provides a hermetic seal between the outer surface and the inner surface.

8. A method according to claim 1, further comprising fixing a mounting flange adjacent to the open end of the hermetic lead connector.

9. A method of manufacturing an implantable active medical device comprising;
providing an active medical device housing defining a housing interior, a power source and electronics in electrical communication are disposed within the housing interior; and
fixing a hermetic lead connector to the active medical device housing, the hermetic lead connector projecting into the housing interior and having an open end projecting through the active medical device housing, the hermetic lead connector comprising an outer surface and an inner surface defining a hermetic lead aperture, the hermetic lead connector comprising one or more electrically conducting contact rings spaced apart and brazed to electrically insulating rings, a fluid seal or wiper seal disposed between adjacent electrically conducting contact rings, the fluid seal or wiper seal assisting in electrically isolating adjacent electrically conducting contact rings; the one or more electrically conducting contact rings in electrical communication with the electronics, and the hermetic lead connector providing a hermetic seal between the hermetic lead connector outer surface and the hermetic lead connector inner surface; wherein the brazing assists in providing a hermetic seal between the lead connector outer surface and the lead aperture.

10. A method according to claim 9, further comprising hermetically sealing the hermetic lead connector within the housing interior to form a hermetically sealed active device housing.

11. A method according to claim 9, further comprising brazing an electrically insulating ring between an electrically conducting contact ring and an electrically conducting spacer ring to form a hermetic ring subassembly, and fixing a plurality of the hermetic ring subassemblies in axial alignment to form a hermetic lead connector.

12. A method according to claim 11, further comprising disposing a fluid seal material on brazed joints within the hermetic ring subassembly before the fixing a plurality of the hermetic ring subassemblies in axial alignment.

13. A method according to claim 11, further comprising disposing a helical annular coil within the hermetic ring subassembly before the fixing of the plurality of the hermetic ring subassemblies in axial alignment.

14. A method according to claim 11, wherein the fixing a plurality of the hermetic ring subassemblies in axial alignment to form a hermetic lead connector comprises fixing a first ring subassembly electrically conducting contact ring to an adjacent second ring subassembly electrically conducting spacer ring.

15. A method according to claim 11, wherein fixing a plurality of the hermetic ring subassemblies in axial alignment to form a hermetic lead connector comprises fixing a plurality of the hermetic ring subassemblies each having substantially similar dimensions in axial alignment to form a hermetic lead connector comprising an open end, an outer surface, and an inner surface defining a lead aperture having a substantially uniform diameter and the hermetic lead connector provides a hermetic seal between the outer surface and the inner surface.

16. A method according to claim 11, wherein the fixing a hermetic lead connector to the active medical device housing step further comprises fixing a mounting flange adjacent to the open end of the hermetic lead connector and then fixing the mounting flange to the active medical device housing.

17. A method of manufacturing an implantable active medical device comprising;
disposing a hermetic lead connector into an active medical device housing, the active medical device housing defining a housing interior, a power source and electronics in electrical communication are disposed within the housing interior, the hermetic lead connector having an open end projecting through the active medical device housing, the hermetic lead connector defining a hermetic lead connector outer surface and a hermetic lead connector inner surface defining a hermetic lead aperture, the hermetic lead connector comprising one or more electrically conducting contact rings brazed to and spaced apart by electrically insulating rings, a fluid seal or wiper seal disposed between adjacent electrically conducting contact rings, the fluid seal or wiper seal assisting in electrically isolating adjacent electrically conducting contact rings; the one or more electrically conducting contact rings in electrical communication with the electronics, and the lead connector providing a hermetic seal between the lead connector outer surface and the lead connector inner surface; wherein the brazing assists in providing a hermetic seal between the lead connector outer surface and the lead aperture.

* * * * *